United States Patent
Heathcote et al.

(10) Patent No.: US 8,513,004 B2
(45) Date of Patent: Aug. 20, 2013

(54) BIOMASS TREATMENT PROCESS

(75) Inventors: John Gervase Mark Heathcote, Cambridgeshire (GB); Marcus Brian Mayhall Fenton, Cambridgeshire (GB)

(73) Assignee: Pursuit Dynamics PLC, Cambridgeshire (GB)

( * ) Notice: Subject to any disclaimer, the term of this patent is extended or adjusted under 35 U.S.C. 154(b) by 165 days.

(21) Appl. No.: 12/451,268

(22) PCT Filed: May 2, 2008

(86) PCT No.: PCT/GB2008/050319
§ 371 (c)(1),
(2), (4) Date: May 14, 2010

(87) PCT Pub. No.: WO2008/135783
PCT Pub. Date: Nov. 13, 2008

(65) Prior Publication Data
US 2010/0233769 A1    Sep. 16, 2010

(30) Foreign Application Priority Data

May 2, 2007   (GB) .................................. 0708482.5
Jun. 5, 2007  (GB) .................................. 0710659.4

(51) Int. Cl.
*C12M 1/00* (2006.01)
(52) U.S. Cl.
USPC ..................................................... 435/300.1
(58) Field of Classification Search
USPC ........... 435/289.1, 290.1, 290.4, 291.1, 300.1
See application file for complete search history.

(56) References Cited

U.S. PATENT DOCUMENTS

| 1,004,770 | A | 10/1911 | Galloway |
| 1,289,812 | A | 12/1918 | Kinney |
| 1,592,448 | A | 7/1926 | Debus |
| 2,083,801 | A | 6/1937 | Eddy |

(Continued)

FOREIGN PATENT DOCUMENTS

| AR | 069254 | 1/2010 |
| CA | 833980 | 2/1970 |

(Continued)

OTHER PUBLICATIONS

Patent Abstracts of Japan, vol. 016, No. 498 (M-1325), Oct. 15, 1992 & JP 04 184000 A (Mitsui Eng & Shipbuild Co Ltd), Jun. 30, 1992.

(Continued)

*Primary Examiner* — Jon P Weber
*Assistant Examiner* — Robert Yamasaki
(74) *Attorney, Agent, or Firm* — Bryan Cave LLP (57) ABSTRACT

A process for the treatment of biomass is provided. The process comprises forming a biomass slurry by mixing biomass with a working fluid, and inducing the biomass slurry to flow through an inlet into a passage. A high velocity transport fluid is injected into the slurry through a nozzle communicating with the passage. The injection of the high velocity transport fluid applies a shear force to the slurry such that the working fluid is atomized and forms a vapor and droplet flow regime, an at least partial vacuum is formed within the passage downstream of the nozzle, and a condensation shock wave is generated within the passage downstream of the nozzle and vacuum by condensation of the transport fluid. An apparatus for treating biomass using the aforementioned process is also provided.

6 Claims, 3 Drawing Sheets

(56) References Cited

U.S. PATENT DOCUMENTS

| | | | |
|---|---|---|---|
| 2,396,290 A | 3/1949 | Schwarz | |
| 2,971,325 A | 2/1961 | Gongwer | |
| 3,259,320 A | 7/1966 | Christian | |
| 3,265,027 A | 8/1966 | Brown | |
| 3,304,564 A | 2/1967 | Green et al. | |
| 3,402,555 A | 9/1968 | Piper | |
| 3,411,301 A | 11/1968 | Olsen | |
| 3,456,871 A | 7/1969 | Gosling | |
| 3,493,181 A | 2/1970 | Goodnight et al. | |
| 3,493,191 A | 2/1970 | Hughes | |
| 3,529,320 A | 9/1970 | Kerns et al. | |
| 3,664,768 A | 5/1972 | Mays et al. | |
| 3,799,195 A | 3/1974 | Hermans | |
| 3,823,929 A | 7/1974 | Rymarchyk | |
| 3,889,623 A | 6/1975 | Arnold | |
| 3,984,504 A | 10/1976 | Pick | |
| 4,014,961 A | 3/1977 | Popov | |
| 4,072,470 A | 2/1978 | Tsuto et al. | |
| 4,101,246 A | 7/1978 | Erickson | |
| 4,157,304 A | 6/1979 | Molvar | |
| 4,175,706 A | 11/1979 | Gerstmann | |
| 4,192,465 A | 3/1980 | Hughes | |
| 4,201,596 A | 5/1980 | Burroughs et al. | |
| 4,212,168 A | 7/1980 | Bouchard et al. | |
| 4,221,558 A | 9/1980 | Santisi | |
| 4,279,663 A | 7/1981 | Burroughs et al. | |
| 4,425,433 A | 1/1984 | Neves | |
| 4,461,648 A | 7/1984 | Foody | |
| 4,487,553 A | 12/1984 | Nagata | |
| 4,659,521 A | 4/1987 | Alleman | |
| 4,718,870 A | 1/1988 | Watts | |
| 4,738,614 A | 4/1988 | Snyder et al. | |
| 4,809,911 A | 3/1989 | Ryan | |
| 4,836,451 A | 6/1989 | Herrick et al. | |
| 4,915,300 A | 4/1990 | Ryan | |
| 4,915,302 A | 4/1990 | Kraus et al. | |
| 5,014,790 A | 5/1991 | Papavergos | |
| 5,061,406 A | 10/1991 | Cheng | |
| 5,138,937 A | 8/1992 | Zietlow | |
| 5,171,090 A | 12/1992 | Wiemers | |
| 5,205,648 A | 4/1993 | Fissenko | |
| 5,240,724 A | 8/1993 | Otto et al. | |
| 5,249,514 A | 10/1993 | Otto et al. | |
| 5,252,298 A | 10/1993 | Jones | |
| 5,269,461 A | 12/1993 | Davis | |
| 5,275,486 A | 1/1994 | Fissenko | |
| 5,312,041 A | 5/1994 | Williams et al. | |
| 5,323,967 A | 6/1994 | Tanaka et al. | |
| 5,338,113 A | 8/1994 | Fissenko | |
| 5,344,345 A | 9/1994 | Nagata | |
| 5,366,288 A | 11/1994 | Dahllof et al. | |
| 5,370,999 A * | 12/1994 | Stuart | 435/99 |
| 5,492,276 A | 2/1996 | Kaylor | |
| 5,495,893 A | 3/1996 | Roberts et al. | |
| 5,520,331 A | 5/1996 | Wolfe | |
| 5,544,961 A | 8/1996 | Fuks et al. | |
| 5,597,044 A | 1/1997 | Roberts et al. | |
| 5,598,700 A | 2/1997 | Varshay et al. | |
| 5,615,836 A | 4/1997 | Graef | |
| 5,661,968 A | 9/1997 | Gabriel | |
| 5,692,371 A | 12/1997 | Varshay et al. | |
| 5,738,762 A | 4/1998 | Ohsol | |
| 5,779,159 A | 7/1998 | Williams et al. | |
| 5,810,252 A | 9/1998 | Pennamen et al. | |
| 5,851,139 A | 12/1998 | Xu | |
| 5,857,773 A | 1/1999 | Tammelin | |
| 5,860,598 A | 1/1999 | Cruz | |
| 5,863,128 A | 1/1999 | Mazzei | |
| 6,003,789 A | 12/1999 | Base et al. | |
| 6,029,911 A | 2/2000 | Watanabe et al. | |
| 6,065,683 A | 5/2000 | Akin et al. | |
| 6,098,896 A | 8/2000 | Haruch | |
| 6,110,356 A | 8/2000 | Hedrick et al. | |
| 6,200,486 B1 | 3/2001 | Chahine et al. | |
| 6,299,343 B1 | 10/2001 | Pekerman | |
| 6,308,740 B1 | 10/2001 | Smith | |
| 6,338,444 B1 | 1/2002 | Swan | |
| 6,371,388 B2 | 4/2002 | Utter et al. | |
| 6,405,944 B1 | 6/2002 | Benalikhoudja | |
| 6,456,871 B1 | 9/2002 | Hsu et al. | |
| 6,478,240 B1 | 11/2002 | Dorkin et al. | |
| 6,502,979 B1 | 1/2003 | Kozyuk | |
| 6,503,461 B1 | 1/2003 | Burgard et al. | |
| 6,523,991 B1 | 2/2003 | Maklad | |
| 6,623,154 B1 | 9/2003 | Garcia | |
| 6,637,518 B1 | 10/2003 | Hillier et al. | |
| 6,662,549 B2 | 12/2003 | Burns | |
| 6,796,704 B1 | 9/2004 | Lott | |
| 6,802,638 B2 | 10/2004 | Allen | |
| 6,830,368 B2 | 12/2004 | Fukano | |
| 6,969,012 B2 | 11/2005 | Kangas et al. | |
| 7,029,165 B2 | 4/2006 | Allen | |
| 7,040,551 B2 | 5/2006 | Rummel | |
| 7,080,793 B2 | 7/2006 | Borisov et al. | |
| 7,111,975 B2 | 9/2006 | Fenton et al. | |
| 7,207,712 B2 | 4/2007 | Kozyuk | |
| 7,667,082 B2 | 2/2010 | Kozyuk | |
| 2002/0162518 A1 | 11/2002 | Dumaz et al. | |
| 2003/0147301 A1 | 8/2003 | Ekholm | |
| 2003/0150624 A1 | 8/2003 | Rummel | |
| 2004/0065589 A1 | 4/2004 | Jorgensen | |
| 2004/0141410 A1 | 7/2004 | Fenton et al. | |
| 2004/0185542 A1 * | 9/2004 | Yang et al. | 435/161 |
| 2004/0188104 A1 | 9/2004 | Borisov et al. | |
| 2004/0222317 A1 | 11/2004 | Huffman | |
| 2005/0000700 A1 | 1/2005 | Sundholm | |
| 2005/0011355 A1 | 1/2005 | Williams et al. | |
| 2005/0150971 A1 | 7/2005 | Zhou | |
| 2005/0266539 A1 | 12/2005 | Hochberg et al. | |
| 2006/0102351 A1 | 5/2006 | Crabtree et al. | |
| 2006/0102749 A1 | 5/2006 | Crabtree et al. | |
| 2006/0144760 A1 | 7/2006 | Duyvesteyn et al. | |
| 2007/0000700 A1 | 1/2007 | Switzer | |
| 2007/0095946 A1 | 5/2007 | Ryan | |
| 2007/0128095 A1 | 6/2007 | Brockmann et al. | |
| 2007/0210186 A1 | 9/2007 | Fenton et al. | |
| 2008/0230632 A1 | 9/2008 | Fenton et al. | |
| 2008/0310970 A1 | 12/2008 | Fenton et al. | |
| 2009/0052275 A1 | 2/2009 | Jansson | |
| 2009/0072041 A1 | 3/2009 | Hashiba | |
| 2009/0240088 A1 | 9/2009 | Fenton et al. | |
| 2009/0314500 A1 | 12/2009 | Fenton et al. | |
| 2010/0085883 A1 | 4/2010 | Zaiser | |
| 2010/0129888 A1 | 5/2010 | Thorup et al. | |
| 2010/0230119 A1 | 9/2010 | Worthy | |
| 2010/0301129 A1 | 12/2010 | Fenton et al. | |
| 2011/0127347 A1 | 6/2011 | Worthy et al. | |
| 2011/0203813 A1 | 8/2011 | Fenton et al. | |
| 2011/0240524 A1 | 10/2011 | Fenton | |

FOREIGN PATENT DOCUMENTS

| | | |
|---|---|---|
| CN | 2356760 | 1/2000 |
| EP | DE 3316233 | 11/1984 |
| EP | 282061 | 3/1988 |
| EP | 0362052 | 10/1991 |
| EP | 0471321 | 11/1995 |
| EP | 0889244 | 1/1999 |
| EP | 0911082 | 4/1999 |
| EP | 1072320 | 1/2001 |
| EP | 1163931 | 12/2001 |
| EP | 1034029 | 3/2003 |
| EP | 1421996 | 5/2004 |
| EP | 1549856 | 6/2007 |
| EP | 2070881 | 6/2009 |
| FR | 474 904 | 3/1915 |
| FR | 1354965 | 3/1964 |
| FR | 2376384 | 7/1978 |
| FR | 2613639 | 10/1988 |
| GB | 995 660 A | 6/1965 |
| GB | 1 028 211 A | 5/1966 |
| GB | 1205776 | 9/1970 |
| GB | 1227444 | 4/1971 |
| GB | 2207952 | 7/1988 |
| GB | 2242370 | 11/1993 |

| | | |
|---|---|---|
| GB | 2313410 | 11/1997 |
| GB | 2384027 | 1/2002 |
| GB | 0223572.9 | 10/2002 |
| GB | 0227053.6 | 11/2002 |
| GB | 0301236.6 | 6/2003 |
| GB | 0404230.5 | 2/2004 |
| GB | 0405363.3 | 3/2004 |
| GB | 0406690.8 | 3/2004 |
| GB | 0407090.0 | 3/2004 |
| GB | 0409620.2 | 4/2004 |
| GB | 0410518.5 | 5/2004 |
| GB | 0416914.0 | 7/2004 |
| GB | 0416915.7 | 7/2004 |
| GB | 0417961.0 | 8/2004 |
| GB | 0428343.8 | 12/2004 |
| GB | 0500580.6 | 1/2005 |
| GB | 0500581.4 | 1/2005 |
| GB | 0618196.0 | 9/2006 |
| GB | 0708482.5 | 5/2007 |
| GB | 0710659.4 | 6/2007 |
| GB | 0710663.6 | 6/2007 |
| GB | 0721995.9 | 11/2007 |
| GB | 0805791.1 | 3/2008 |
| GB | 0806182.2 | 4/2008 |
| GB | 0810155.2 | 6/2008 |
| GB | 0818362.6 | 10/2008 |
| JP | 03-260405 | 11/1991 |
| JP | 2004-184000 | 6/1992 |
| JP | 10-141299 | 5/1998 |
| JP | 10-226503 | 8/1998 |
| JP | 2001-354319 | 12/2001 |
| JP | 2003-515702 | 5/2003 |
| JP | 0803959.6 | 3/2008 |
| NL | 7409053 | 1/1975 |
| RU | 2142580 | 12/1999 |
| RU | 2152465 | 7/2000 |
| SU | 1653853 | 6/1991 |
| SU | 2040322 | 5/1992 |
| TW | 200940124 | 10/2009 |
| WO | WO 89/07204 | 8/1989 |
| WO | WO 89/10184 | 11/1989 |
| WO | WO 92/20453 | 11/1992 |
| WO | WO 92/20454 | 11/1992 |
| WO | WO 94/08724 | 4/1994 |
| WO | WO 97/00373 | 1/1997 |
| WO | WO 97/38757 | 10/1997 |
| WO | PCT/US98/005275 | 3/1998 |
| WO | PCT/RU97/000299 | 9/1998 |
| WO | WO 00/02653 | 1/2000 |
| WO | WO 00/71235 | 1/2000 |
| WO | WO 00/09236 | 2/2000 |
| WO | PCT/RU00/000118 | 4/2000 |
| WO | WO 00/37143 | 6/2000 |
| WO | WO 01/36105 | 5/2001 |
| WO | WO 01/76764 | 10/2001 |
| WO | WO 01/94197 | 12/2001 |
| WO | WO 03/030995 | 4/2003 |
| WO | WO 03/061769 | 7/2003 |
| WO | WO 03/072952 | 9/2003 |
| WO | WO 2004/033920 | 4/2004 |
| WO | WO 2004/038031 | 6/2004 |
| WO | WO 2004/057196 | 7/2004 |
| WO | PCT/GB2005/000708 | 2/2005 |
| WO | PCT/GB2005/000720 | 2/2005 |
| WO | WO 2005/082546 | 9/2005 |
| WO | WO 2005/115555 | 12/2005 |
| WO | WO 2005/123263 | 12/2005 |
| WO | WO 2006/010949 | 2/2006 |
| WO | WO 2006/024242 | 3/2006 |
| WO | WO 2006/034590 | 4/2006 |
| WO | WO 2006/132557 | 12/2006 |
| WO | WO 2007/037752 | 4/2007 |
| WO | PCT/GB2007/003492 | 9/2007 |
| WO | WO 2008/062218 | 5/2008 |
| WO | PCT/GB2008/01883 | 6/2008 |
| WO | PCT/GB2008/051042 | 11/2008 |
| WO | PCT/US08/012571 | 11/2008 |
| WO | WO 2008/135775 | 11/2008 |
| WO | WO 2008/135783 | 11/2008 |
| WO | WO 2009/060240 | 5/2009 |
| WO | PCT/GB2009/050626 | 6/2009 |
| WO | WO 2009/147443 | 12/2009 |
| WO | WO 2010/003090 | 1/2010 |
| WO | WO 2010/041080 | 4/2010 |
| WO | WO 2010/049815 | 5/2010 |

OTHER PUBLICATIONS

Patent Abstracts of Japan, vol. 2002, No. 4, Aug. 4, 2002 & JP 2001 354319 A (Ogawa Jidosha:KK), Dec. 25, 2001.
Final Scientific Report, "New Regenerative Cycle for Vapor Compression Refrigeration", DE-FG36-04GO14327.
Cincotta, "From the Lab to Production: Direct Steam Injection Heating of Fibrous Slurries", Biomass Magazine, Jul. 1, 2008.
Khanal, et al., "Ultrasound Enhanced Glucose Release From Corn in Ethanol Plants", Biotechnology and Bioengineering, vol. 98, No. 5, pp. 978-985, Dec. 1, 2007.
Hagen, Energy economy by continuous steaming and mashing, International Food Information Service (IFIS), Frankfurt-Main, DE (1984).
Arvidson, et al., The VINNOVA water mist research project: A description of the 500 m3 machinery space tests, SP Swedish National Testing and Research Institute, SP Fire Technology, SP Report 2003:19.
Dlugogorski, et al., Water Vapour as an Ineiting Agent, Halon Options Technical Working Conference, pp. 7-18 (May 6-8, 1997).
High pressure water mist for efficient fire protection, Engineer Live (Oct. 8, 2007).
Kim, Andrew, Overview of Recent Progress in Fire Suppression Technology, Institute for Research in Construction, NRCC-45690. Invited Keynote Lecture of the $2^{nd}$ NRIFD Symposium, Proceedings, Tokyo, Japan, Jul. 17-19, 2002, pp. 1-13.
Liu, et al., A Review of water mist fire suppression systems—fundamental studies, National Research Council Canada (2000).
Liu, et al., A Review of water mist fire suppression technology: Part II—Application studies, National Research Council Canada (Feb. 2001).
Liu, et al., Review of Three Dimensional Water Fog Techniques for Firefighting, National Research Council Canada (Dec. 2002).
Mawhinney, et al., A State-of-the-Art Review of Water Mist Fire Suppression Research and Development—1996, National Research Council Canada (Jun. 1996).
Mawhinney, et al., Report of the Committee on Water Mist Fire Suppression Systems, NFPA 750, pp. 141-147 (Nov. 2002 ROC).
PDX® FireMist Comparative Data, Pursuit Dynamics pic (Jul. 1, 2005).
Schlosser, et al., In Situ Determination of Molecular Oxygen Concentrations in Full Scale Fire Suppression Tests Using TDLAS, The 2nd Joint Meeting of the US Sections of the Combustion Institute, Oakland, CA (Mar. 28, 2001).
Vaari, A Study of Total Flooding Water Mist Fire Suppression System Performance using a Transient One-Zone Computer Model, Fire Technology, 37, 327-342 (2001).
Patent Abstracts of Japan, JP 03-260405, published Nov. 20, 1991.
Machine English language translation by EPO of FR 1354965, Mar. 13, 1964.

* cited by examiner

BIOMASS TREATMENT PROCESS

This application is a U.S. National Stage Application of International Application No. PCT/GB2008/050319, which was filed on May 2, 2008, and which claims priority to Great Britain Application Nos. 0708482.5, which was filed on May 2, 2007, and 0710659.4, filed Jun. 5, 2007. The present application also claims benefit, as a continuation-in-part, to U.S. application Ser. No. 11/658,265 filed Jan. 24, 2007, which is the national stage of International application no. PCT/GB2005/02999, which was filed on Jul. 29, 2005 and claims benefit to GB 0416914.0; GB 0416915.7; GB 0417961.0 and GB 0428343.8, dated 29 Jul. 2004; 29 Jul. 2004; 12 Aug. 2004 and 24 Dec. 2004, respectively. All of the foregoing applications are incorporated by reference in their entireties as if recited in full herein.

The present invention relates to the processing of biomass for the purpose of producing biofuels. The invention may be used in various processes used in biofuel production and is particularly suited, although not exclusively so, to the pre-treatment of lignocellulosic biomass and fermentation of sugars into alcohol.

The conversion of biomass into biofuel has taken on great significance in recent years as consumers and producers alike recognise the environmental and sustainability issues surrounding existing fossil fuels. The bulk of existing biofuel is derived from the fermentation of sugar crops and crops having a high starch content, but these crops have a high value in food applications and their sugar yield per hectare is low when compared to the potential sugar yield from cellulose and hemicellulose crops. Thus, the derivation of biofuel from alternative sources of biomass, such as lignocellulosic biomass composed primarily of lignin, hemicellulose and cellulose, is of great significance to producers.

Lignocellulosic biomass is an extremely abundant biomass. It includes all trees and grasses, as well as agricultural residues such as wet and dry distiller's grains, corn fibre, corn cob and sugarcane bagasse. Lignocellulosic biomass can be converted into ethanol by hydrolysis and subsequent fermentation. In hydrolysis, the cellulosic part of the biomass is converted to sugars, and the fermentation converts these sugars to ethanol. To increase the yield of the hydrolysis, a pre-treatment step is needed to soften the biomass and disrupt its cellular structure, thereby exposing more cellulose and hemicellulose material.

Disruptive pre-treatment processes are normally chemical or physical in nature. Current chemical pre-treatment processes rely on a catalyst to achieve the desired disruption of the cells of the biomass. This catalyst is commonly an acid or an enzyme. The acid has the disadvantage of being harmful to the environment, whilst enzymes are relatively expensive. The most common physical pre-treatment process is steam explosion, examples of which are disclosed in U.S. Pat. No. 4,425,433 and U.S. Pat. No. 4,461,648. In steam explosion, the biomass is heated using high pressure steam for a few minutes, before the reactions are stopped by a sudden decompression to atmospheric pressure. A disadvantage of steam explosion is that the process must be contained within a suitable process vessel, and is thus a non-continuous process. Furthermore, the sugar yields from steam explosion are comparatively low while current costs for the process are high.

Once the sugars have been extracted from the biomass material, the sugars are fermented in order to obtain alcohol. Conventional processes use yeast to ferment the sugars, but the yeast is temperature sensitive and the biomass must be cooled to around 30° C. before the yeast can ferment the sugars. Cooling the biomass not only increases the length of the fermentation process, but also increases energy consumption given that the fermented biomass must be re-heated downstream for distillation.

It is an aim of the present invention to obviate or mitigate one or more of the aforementioned disadvantages present in existing biofuel production processes.

According to a first aspect of the present invention, there is provided a process for the treatment of biomass, comprising:
  forming a biomass slurry by mixing biomass with a working fluid;
  inducing the biomass slurry to flow through an inlet into a passage; and
  injecting a high velocity transport fluid into the slurry through a nozzle communicating with the passage;
  wherein the injection of the high velocity transport fluid:
    applies a shear force to the slurry such that the working fluid is atomised and forms a vapour and droplet flow regime;
    forms an at least partial vacuum within the passage downstream of the nozzle; and
    generates a condensation shock wave within the passage downstream of the nozzle and vacuum by condensation of the transport fluid.

Where the term "biomass slurry" is used in this patent specification, it should be understood that the term describes any slurry formed from a working fluid and biomass material. Non-limiting examples of suitable types of biomass material include forest products, untreated wood products, energy crops and short rotation coppice, as well as animal waste, industrial and biodegradable municipal products from food processing and high energy crops such as rape, sugar cane, and maize.

Preferably, the transport fluid is steam.

Preferably, the transport fluid is injected at a supersonic velocity.

Preferably, the passage is of substantially constant diameter. Preferably the nozzle is an annular nozzle which circumscribes the passage.

Preferably, the process is a batch process in which the processed slurry is returned to the inlet. Alternatively, the process is an in-line process in which the inlet receives slurry from an upstream portion of a biofuel production line, and the passage passes the processed slurry to a downstream portion of the production line.

Preferably, the process further comprises the step of injecting a first catalyst into the slurry. Alternatively, the process further comprises the step of injecting first and/or second catalysts into the slurry. The first and second catalysts may be injected simultaneously or consecutively. Where the process is a batch process and the catalysts are to be injected consecutively, the first catalyst is injected into the slurry for a first period of time, and the second catalyst is injected into the slurry for a second period of time occurring after the first period has elapsed.

Preferably, the first and/or second catalysts are injected into the slurry as it passes through the partial vacuum within the passage.

Preferably the first catalyst is an acid. Preferably the second catalyst is an enzyme.

Alternatively, the first catalyst is a gas. Most preferably, the gas is carbon dioxide or air.

Preferably, the biomass is lignocellulosic biomass.

In one embodiment of the invention, the process further comprises a fermentation step in which one or more types of thermophilic micro-organism are introduced into the biomass slurry to convert sugars present into alcohol.

Preferably, the process further includes the steps of:

vapourising the alcohol in the slurry as it passes through the partial vacuum; and separating the alcohol vapour from the remaining slurry.

Preferably, the separation step is achieved by utilising an in-line separation mechanism. Most preferably, the separation mechanism is a vortex separator.

According to a second aspect of the invention, there is provided a biomass treatment apparatus, comprising:

a mixing container adapted to mix a supply of biomass and a supply of working fluid to form a biomass slurry;

a pump adapted to pump the slurry from the mixing container; and at least one fluid processor adapted to receive the slurry from the mixing container;

wherein the fluid processor comprises:

a fluid passage having a passage inlet in fluid communication with the mixing container and a passage outlet; and a transport fluid nozzle opening into the passage intermediate the inlet and the outlet, the nozzle adapted to inject a high velocity transport fluid into passage.

Preferably, the apparatus comprises a plurality of fluid processors in series with one another.

Preferably, the apparatus further comprises at least one back pressure valve located downstream of the passage outlet. Most preferably, the apparatus further comprises a pair of back pressure valves located downstream of the passage outlet.

Preferably, the apparatus further comprises at least one additive port adapted to introduce one or more additives to the fluid passage. In one embodiment, the additive port is located intermediate the mixing container and the fluid passage inlet.

In an alternative embodiment, the additive port is located adjacent the transport fluid nozzle. Most preferably, the additive port is located immediately downstream of the transport fluid nozzle.

In one embodiment, the apparatus further comprises a recirculation circuit which is adapted to return slurry from the fluid passage outlet to the mixing container. The at least one back pressure valve is located in the recirculation circuit.

In an alternative embodiment, the apparatus further comprises a holding vessel located downstream of the fluid passage outlet. The at least one back pressure valve is located intermediate the fluid passage outlet and the holding vessel.

The apparatus preferably further comprises a plurality of sensors adapted to measure pressure upstream and downstream of the fluid processor.

The apparatus preferably further comprises a plurality of sampling ports upstream and downstream of the fluid processor, the sampling ports adapted to allow fluid samples to be removed from the apparatus.

Preferably, the mixing container includes agitation means for mixing the contents thereof.

Preferably, the pump is a progressive cavity pump.

Preferably, the fluid passage is of substantially constant diameter.

Preferably, the transport fluid nozzle is annular and circumscribes the fluid passage.

The apparatus may further comprise a vapour separation mechanism adapted to separate vapour from the remaining fluid. Preferably, the separation mechanism is an in-line separator. Most preferably, the separation mechanism is a vortex separator.

A preferred embodiment of the present invention will now be described, by way of example only, with reference to the accompanying drawings, in which.

Figure 1:
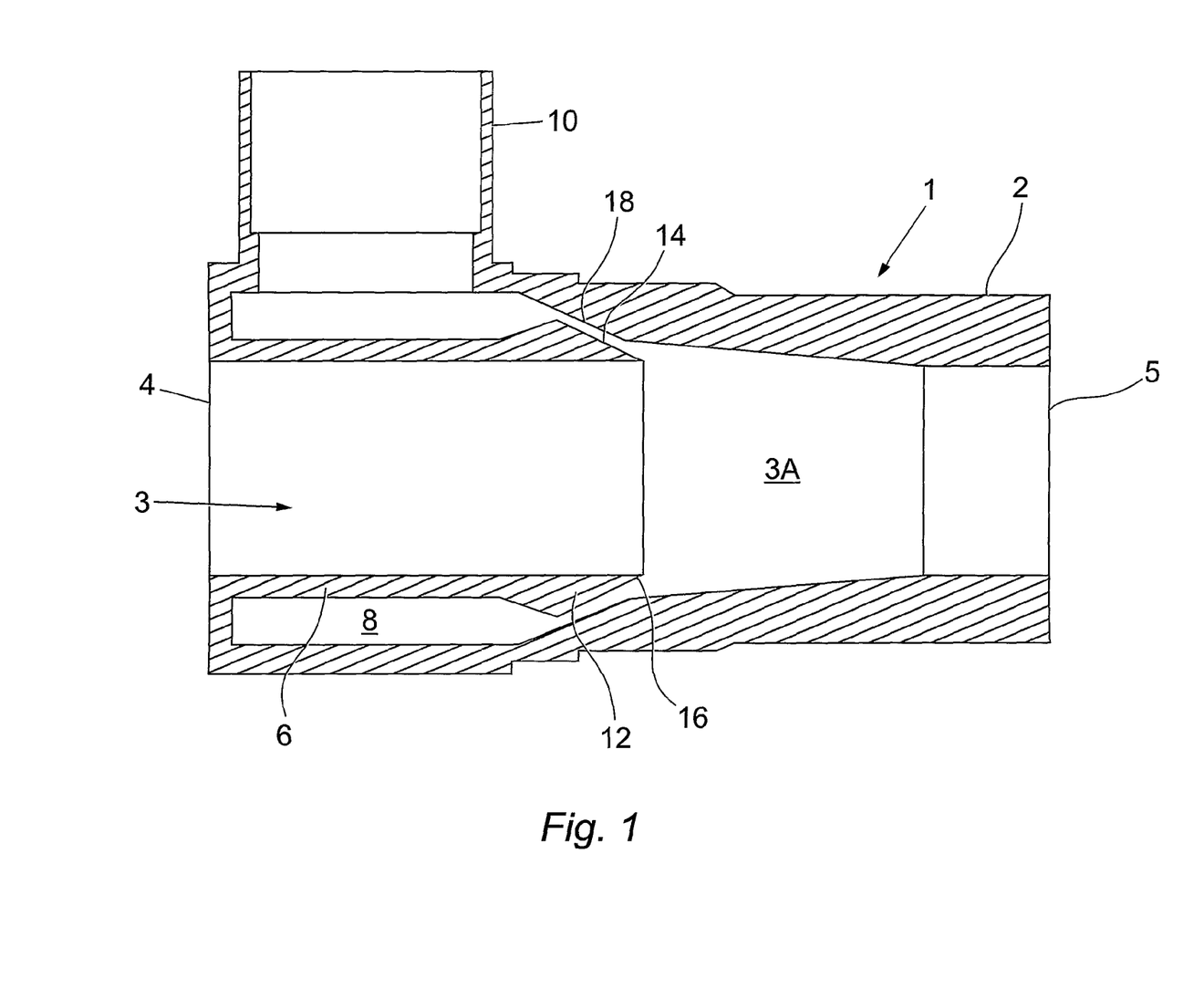
FIG. 1 shows a cross-section through a fluid processor suitable for use in the process of the present invention.

Referring to FIG. 1 there is shown a fluid processor 1 comprising a housing 2 defining a passage 3 providing an inlet 4 and an outlet 5. Preferably, the passage 3 is of substantially constant circular cross section. The inlet 4 is formed at the front end of a protrusion 6 extending into the housing 2 and defining exteriorly thereof a plenum 8 for the introduction of a transport fluid, the plenum 8 being provided with an inlet 10. The protrusion 6 defines internally thereof part of the passage 3. The distal end 12 of the protrusion 6 remote from the inlet 4 is tapered on its relatively outer surface at 14 and defines a nozzle 16 between it and a correspondingly tapered part 18 of the inner wall of the housing 2. The nozzle 16 is in flow communication with the plenum 8 and is preferably annular. The nozzle 16 has convergent-divergent internal geometry in order to accelerate the transport fluid to a high velocity. In other words, the nozzle 16 has a throat portion which has a smaller cross-sectional area than that of either the nozzle inlet or nozzle outlet.

Whether the process is a batch or in-line process, the inlet 4 receives a biomass slurry which passes out of the outlet 5. Introduction of the transport fluid, which in this non limiting example is steam, into the fluid processor 1 through the inlet 10 and plenum 8 causes a jet of steam to issue forth through the nozzle 16. As the steam is injected into the slurry, a momentum and mass transfer occurs between the two which results in the atomisation of the working fluid component of the slurry. This transfer is enhanced through turbulence. The steam applies a shearing force to the slurry which not only atomises the working fluid component but also disrupts the cellular structure of the lignocellulosic biomass suspended in the slurry.

Figure 2:
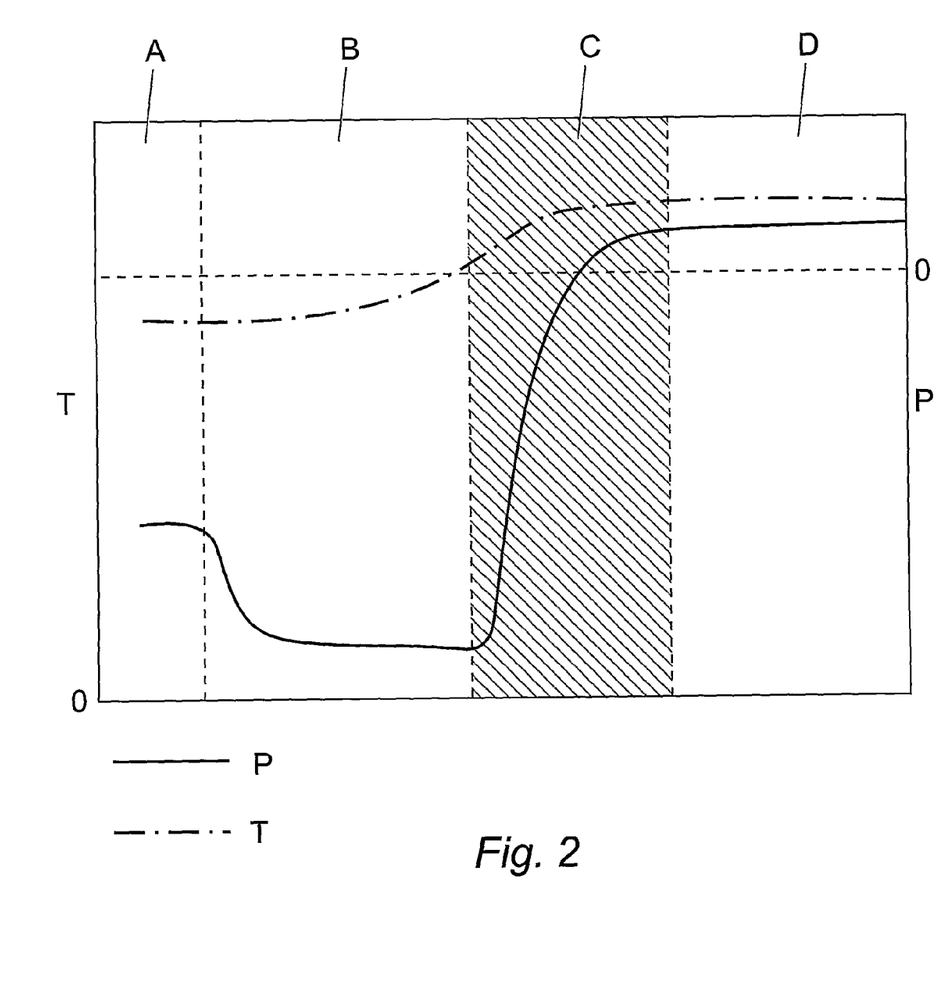
FIG. 2 shows a graph showing pressure and temperature profiles of a biomass slurry as it passes through the fluid processor.

The effects of the process on the temperature and pressure of the slurry can be seen in the graph of FIG. 2, which shows the profile of the temperature and pressure as the slurry passes through various points in the fluid processor of FIG. 1. The graph has been divided into four sections A-D, which correspond to various sections of the fluid processor shown in FIG. 1. Section A corresponds to the section of the passage 3 between the inlet 4 and the nozzle 16. Section B corresponds to the upstream section of the mixing chamber 3A extending between the nozzle 16 and an intermediate portion of the chamber 3A. Section C corresponds to a downstream section of the mixing chamber 3A extending between the aforementioned intermediate portion of the chamber 3A and the outlet 5, while section D illustrates the temperature and pressure of the slurry as it passes through the outlet 5.

The steam is injected into the slurry at the beginning of section B of the FIG. 2 graph. The speed of the steam, which is preferably injected at a supersonic velocity, and its expansion upon exiting the nozzle 16 cause an immediate pressure reduction. At a point determined by the steam and geometric conditions, and the rate of heat and mass transfer, the steam begins to condense, further reducing the pressure and causing a further increase in temperature. The steam condensation continues and forms a condensation shock wave in the downstream section of the mixing chamber 3A. The forming of a condensation shock wave causes a rapid increase in pressure, as can be seen in section C of FIG. 2. Section C also shows that the temperature of the slurry also continues to rise through the condensation of the steam.

As explained above, as the steam is injected into the slurry through nozzle 16 a pressure reduction occurs in the upstream section of the mixing chamber 3A. This reduction in pressure forms an at least partial vacuum in this upstream section of the chamber 3A. Tests have revealed that an approximately 90% vacuum can be achieved in the chamber 3A as the steam is injected and subsequently condenses.

As previously stated, the shear force applied to the slurry and the subsequent turbulent flow created by the injected steam disrupts the cellular structure of the biomass suspended in the slurry. As the slurry passes through the partial vacuum and condensation shock wave formed in the chamber 3A, it is further disrupted by the changes in pressure occurring, as illustrated by the pressure profile in sections B and C of FIG. 2.

Figure 3:
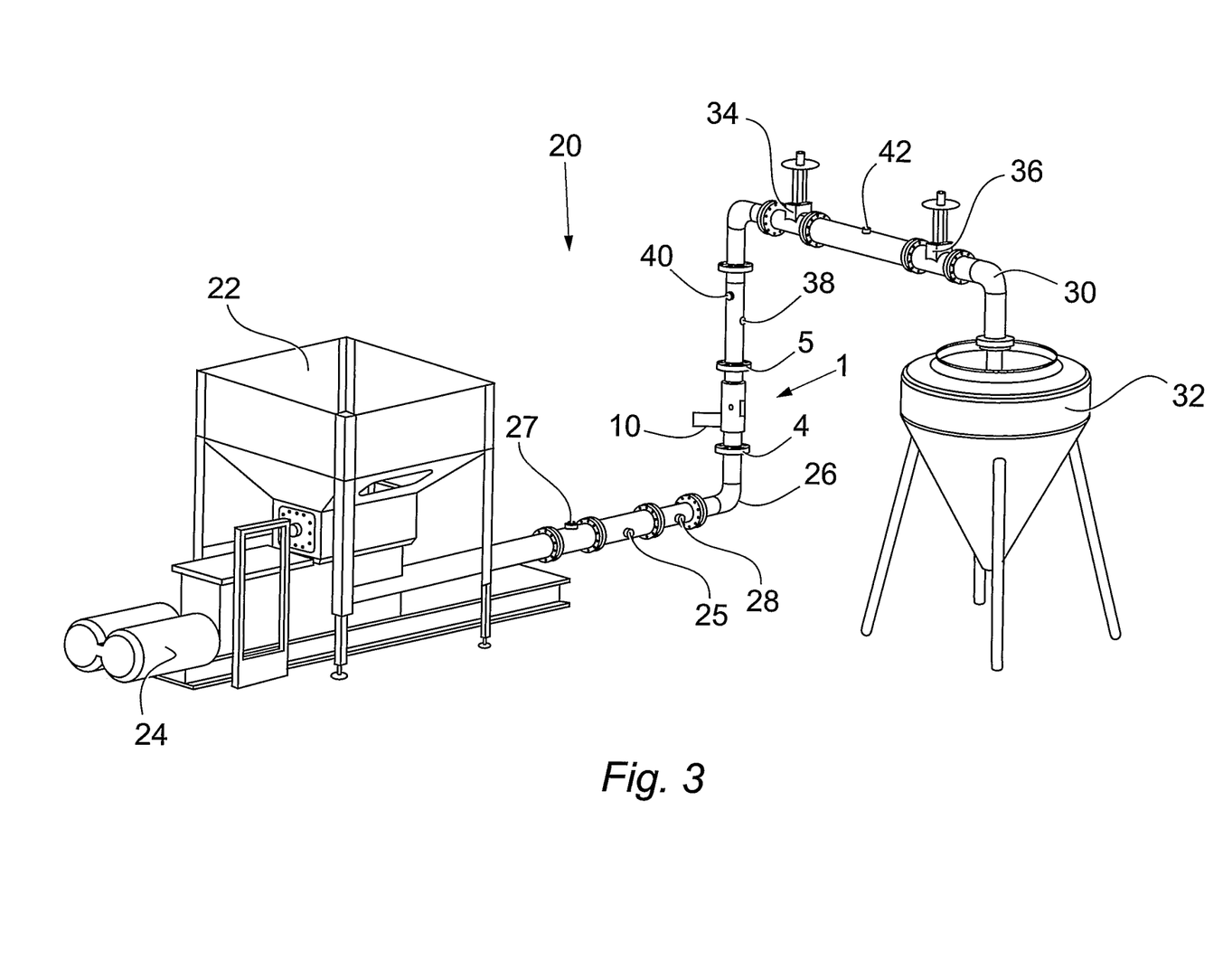
FIG. 3 shows a processing apparatus incorporating the fluid processor of FIG. 1.

FIG. 3 shows an example arrangement of a biofuel treatment apparatus, generally designated 20, which incorporates the fluid processor 1 shown in FIG. 1. The illustrated embodiment shows the apparatus in an in-line configuration. In other words, the apparatus shown is intended to treat the biomass slurry in a single pass through the apparatus.

A first hopper 22 operating as a mixing container is located at an upstream end of the apparatus 20. The hopper 22 contains an agitator (not shown) for stirring the contents of the hopper 22. Positioned beneath the hopper 22 and in fluid communication therewith is a solids-handling pump 24, which is adapted to pump the contents of the hopper 22 to the remainder of the apparatus 20. The pump 24 is preferably a progressive cavity pump, otherwise known as rotary positive displacement pump.

The outlet of the pump 24 is connected by pipework 26 to the inlet 4 of the fluid processor 1. If desired, the pipework 26 upstream of the processor 1 can incorporate a catalyst additive port 25, as well as a first pressure sensor 27 and/or a first sampling port 28.

As described above with reference to FIG. 1, the inlet 10 supplies transport fluid to the processor 1. The outlet 5 of the processor 1 is connected to a further length of pipework 30, which in the illustrated in-line configuration connects the processor 1 to a second hopper, or holding vessel, 32. Located in the pipework 30 between the processor 1 and the second hopper 32 are first and second back pressure valves 34,36. If desired, a second pressure sensor 38 and/or a second sampling port 40 can be located between the processor 1 and the first back pressure valve 34. A third pressure sensor 42 can be located between the first and second back pressure valves 34,36.

The method of operation of the treatment apparatus 20 will now be described with reference again to FIG. 3. Biomass material and a suitable working fluid are initially combined in the first hopper 22 in order to form a biomass slurry. The agitator located in the hopper 22 ensures that the components are thoroughly mixed and the biomass is adequately hydrated. Once the components have undergone sufficient mixing and the biomass is adequately hydrated, the pump 24 is activated. Once activated, the pump 24 gently pumps the slurry through the pipework 26 towards the fluid processor 1. If required, a catalyst which assists in the cellular disruption of the biomass can be introduced into the slurry via the additive port 25 as the slurry is pumped and induced through the pipework 26.

A supply of transport fluid is supplied to the fluid inlet 10 of the fluid processor 1. In the fluid processor 1, the high pressure transport fluid is injected into the slurry in the manner described above with reference to FIG. 1. Following the formation of a vapour and droplet flow regime, the slurry will condense back into liquid form before leaving the processor 1. The condensed slurry then passes into the second hopper 32, where it will undergo a further step in the biofuel process such as liquefaction, for example.

The first, second and third pressure sensors 27,38,42 allow the fluid pressure in the pipework 26,30 to be monitored both upstream and downstream of the fluid processor 1. The first and second back pressure valves 34,36 can be adjusted to vary the pressure in the pipework 30 downstream of the processor 1 depending on the readings from the second and third pressure sensors 38,42. The back pressure valves 34,36 allow the slurry to be held at an elevated pressure for a longer period of time. The first and second sampling ports 28,40 allow tests to be carried out on samples of the slurry both before and after it passes through the fluid processor 1.

The catalyst which can be added by way of the additive port may be an acid or a gas. Adding a gas into the slurry can alter the pH of the slurry and, where the gas is pressurised, it can go into solution in the slurry and explode out as the slurry passes through the partial vacuum in the mixing chamber of the fluid processor. An example of a suitable gas for this purpose is carbon dioxide ($CO_2$). Air may also be used as a catalyst in the slurry. Air is used in order to achieve supersaturation of its constituent gases in the slurry. The excess gas in the slurry leads to the formation of gas bubbles in the cellular structure of the biomass, which in turn has a disruptive effect on the cellular structure of the biomass through the phenomenon known as gas bubble trauma.

A further catalyst, such as an enzyme, may also be added via the additive port or else directly into the second hopper. The enzyme may assist pre-treatment or else may be required for the later stages of the biofuel process (e.g. liquefaction enzymes). Unlike in existing pre-treatment processes, the comparatively low temperature and pressure used in the fluid processor will not kill the enzymes during the disruption stage. Thus, the enzymes needed later in the biofuel production process can be added before pre-treatment without them being damaged.

During a trial processing sugarcane bagasse there was evidence of wall swelling in the cellular structure of the biomass. This is an indication that the crystalline structure of the cellulose was disrupted during the inventive process. This swelling of the cellulose facilitates the action of cellulose enzymes and therefore accelerates the subsequent hydrolysis process and/or increases the yield of fermentable sugars. This effect could be interpreted as a swelling resulting from scission of hydrogen bonds as a result of the shear forces and mechanical shock caused by the process.

By injecting steam into the biomass slurry in such a way as to atomise the working fluid and create a partial vacuum and condensation shock wave through which the slurry passes, the present invention ensures a greater degree of disruption to the cellular structure of the biomass than that achieved by existing pre-treatment processes. Furthermore, as the disruption is at least partially achieved by the steam injection, the invention enables a reduced amount of catalyst or additive to obtain the desired degree of disruption when compared with existing chemical pre-treatment processes. In fact, the disruption achieved by the steam injection may remove the need for one or more catalysts entirely. The steam injection of the present process ensures continual shearing of the slurry and maintains the partial vacuum and shock wave. The process of the present invention is therefore continuous, with no need to contain the process in a stand-alone vessel such as that required in steam explosion processes.

Similarly, injecting the catalysts into the partial vacuum created in the process allows the catalysts a higher level of penetration into the biomass. Thus, either a lesser amount of catalyst can be used, or else the same amount of catalyst can be used as in the existing processes with an improved degree or rate of disruption.

The high shear forces imparted by the high velocity steam injection not only assist in the disruption of the cellular structure of the biomass, but also atomise the working fluid component of the slurry to ensure intimate and homogenous heating and mixing of the biomass slurry with the catalysts. Such improved heating and mixing reduces the amount of time and catalyst required to achieve the necessary chemical reaction.

The present invention also provides advantages when used in the fermentation stage of biofuel production. Once sugars have been extracted from the biomass material, the biomass slurry is then fermented to convert the sugar to alcohol. Conventional processes use yeast to provide the fermentation stage. Current yeast technology requires temperatures around 30° C., which means that the biomass must be cooled between the hydrolysis and fermentation stages. This has an impact on the time and cost of the production process, as the cooling delays the process whilst having to re-heat the fermented slurry before distillation increases energy consumption.

Thermophilic micro-organisms are able to tolerate temperatures much higher than 30° C. (e.g. 60-80° C.) when converting sugars present in biomass slurry into alcohol. When being used for fermentation the process of the present invention is modified to include the step of introducing one or more types of thermophilic micro-organisms into the biomass slurry as a catalyst. Preferably, where the process is an in-line process the thermophilic micro-organisms are added prior to the injection of the high velocity transport fluid into the slurry.

The process of the present invention can also be used as an enhanced separator of the alcohol following fermentation. As the fermented slurry is subjected to the process of the present invention, the liquid alcohol portion transfers into a gas form within the partial vacuum created by the inventive process. This provides an opportunity to extract the alcohol vapour from the remaining fluids and solids as soon as it is created. An in-line separation mechanism may be used downstream of the partial vacuum to effect the removal of the alcohol vapour. A vortex separator may be used as the separation mechanism.

The separation mechanism may be configured such that the internal pressure and temperature still allow the steam condensation to occur, while maintaining the alcohol in the vapour phase. This allows easier separation of the vapour from the much higher density liquids and solids in the process flow. This process may remove, or at least shorten, the distillation stage needed in conventional processes.

A limitation of current fermentation processes is that the fermented biomass slurry contains an azeotrope. It is known that azeotropes can be affected by pressure, as pressure changes can have an effect on the vapour-liquid equilibrium compositions of azeotropic mixtures. The pressure changes provided by the inventive process of the present invention assist in the disruption of the azeotrope, thereby further enhancing the extraction of alcohol.

The process of the present invention accelerates the fermentation reaction by providing heat, low thermal shock, and homogenous mixing of the thermophilic micro-organisms with the sugars.

Thermophilic micro-organisms have the potential to significantly speed up the fermentation stage of the process. In addition, use of thermophilic micro-organisms has the potential to improve the efficiency and cost effectiveness of biofuel production. Part of the cost savings come from the energy savings gained from removing the need to cool down the biomass for the fermentation stage, and then heat back up for the downstream distillation stage.

Whilst steam is the preferred transport fluid used in the process of the present invention, it should be understood that other suitable fluids may also be used instead.

Although not shown in either FIG. 1 or FIG. 3, one or more additive ports may be provided immediately downstream of the transport fluid nozzle 16, either in addition to or instead of the additive port upstream of the fluid processor. These ports would open into the upstream section of the mixing chamber 3A where the vacuum is formed during the processing operation. A single port can be connected to a supply of one or more of the catalysts described above, which can be injected into the slurry to further disrupt the cellular structure of the biomass. Wherever the ports are located, the injection of the catalyst(s) into the partial vacuum can be timed for a specific period to achieve a specific dosage. Where a single port is used, it may be connected to sources of separate catalysts and can inject either or both.

Alternatively, a pair of additive ports can be used to inject the catalysts into the partial vacuum, either simultaneously or consecutively. In the instance where the process forms part of a biofuel production line, the pair of ports will inject the catalysts simultaneously.

The additive port(s) may also inject an enzyme only, with no acids being used.

The additive ports can also include a control means which monitors the flow rate of the slurry through the passage and meters the dosage of catalyst introduced by the nozzle(s).

In the in-line embodiment of the present invention, a number of fluid processor units may be placed in series. In this instance, units can be used to heat the slurry to a higher temperature than a single unit. Alternatively, the multiple units can be used for differing purposes. For example, a first unit can apply the process of the present invention and inject a chemical pre-treatment catalyst while a subsequent unit can apply the process again but introduce an enzyme. Catalysts may be introduced through one or more of the units in the series.

Whilst the example of the processing apparatus illustrated in FIG. 3 was shown in an in-line configuration, it should be recognised that the apparatus can also be placed in a recirculation configuration. In the recirculation configuration the pipework downstream of the fluid processor would return to the first hopper instead of carrying the slurry downstream to a second hopper. A suitable outlet valve is provided in the apparatus when in the recirculation configuration to allow the treated slurry to be removed from the apparatus.

As well as mixing the slurry components together, the first hopper may also be provided with heating means in order to heat the slurry and insulating means to hold it at a suitable temperature. Alternatively, the working fluid component of the slurry may be heated at a remote location, and the first hopper provided just with insulating means. This process of holding the slurry at an elevated temperature for a period of time is known as "steeping".

Other modifications and improvements may be incorporated without departing from the scope of the invention.

The invention claimed is:

1. A biomass treatment apparatus, comprising:
   a mixing container adapted to mix a supply of biomass and a supply of working fluid to form a biomass slurry;
   a pump adapted to pump the slurry from the mixing container; and
   at least one fluid processor adapted to receive the slurry from the mixing container;
   wherein the fluid processor comprises:
   a hollow body provided with a straight-through passage of substantially constant cross section with an inlet at one end of the passage and an outlet at the other end of the passage for the entry and discharge respectively of a working fluid;

a nozzle substantially circumscribing and opening into said passage intermediate the inlet and outlet ends thereof;

an inlet communicating with the nozzle for the introduction of a transport fluid; and a mixing chamber being formed within the passage downstream of the nozzle;

wherein an internal wall of the passage upstream of the mixing chamber is provided with at least one groove that creates turbulence in the working fluid flow prior to any interaction between the working fluid and the transport fluid; and wherein the nozzle internal geometry, the bore profile of the passage immediately upstream of the nozzle exit and the internal wall of the straight-through passage are so disposed and configured to optimise the energy transfer between the transport fluid and working fluid that in use through the introduction of transport fluid the working fluid or fluids are atomised to form a dispersed vapour/droplet flow regime with locally supersonic flow conditions within a pseudo-vena contracta, resulting in the creation of a supersonic condensation shock wave within the downstream mixing chamber by the condensation of the transport fluid.

2. The apparatus of claim 1, comprising a plurality of fluid processors in series with one another.

3. The apparatus of claim 1 further comprising at least one additive port adapted to introduce one or more additives to the fluid passage.

4. The apparatus of claim 1 further comprising a recirculation circuit which is adapted to return slurry from the fluid passage outlet to the mixing container.

5. The apparatus of claim 1 further comprising a plurality of sensors adapted to measure pressure upstream and downstream of the fluid processor.

6. The apparatus of claim 1, wherein the transport fluid nozzle is annular and circumscribes the fluid passage.

* * * * *